(12) United States Patent
Ludescher et al.

(10) Patent No.: US 7,884,205 B2
(45) Date of Patent: Feb. 8, 2011

(54) SALTS OF ARIPIPRAZOLE

(75) Inventors: Johannes Ludescher, Breitenbach (AT); Hubert Sturm, Innsbruck (AT)

(73) Assignee: Sandoz AG, Basel (CH)

( * ) Notice: Subject to any disclaimer, the term of this patent is extended or adjusted under 35 U.S.C. 154(b) by 396 days.

(21) Appl. No.: 11/883,125

(22) PCT Filed: Jan. 27, 2006

(86) PCT No.: PCT/EP2006/000726

§ 371 (c)(1),
(2), (4) Date: Apr. 14, 2008

(87) PCT Pub. No.: WO2006/079549

PCT Pub. Date: Aug. 3, 2006

(65) Prior Publication Data

US 2008/0287677 A1    Nov. 20, 2008

(30) Foreign Application Priority Data

Jan. 27, 2005 (EP) .................................. 05001638
Jan. 27, 2005 (EP) .................................. 05001639

(51) Int. Cl.
*C07D 401/12* (2006.01)
*A61K 31/497* (2006.01)
(52) U.S. Cl. ................................. 544/363; 514/253.13
(58) Field of Classification Search ................ 544/363; 514/253.13
See application file for complete search history.

(56) References Cited

U.S. PATENT DOCUMENTS

| 4,734,416 A | 3/1988 | Banno et al. |
| 5,006,528 A | 4/1991 | Oshiro et al. |
| 2005/0159429 A1 | 7/2005 | Parthasaradhi et al. |

FOREIGN PATENT DOCUMENTS

WO    WO 2004106322    12/2004

*Primary Examiner*—James O Wilson
*Assistant Examiner*—Ebenezer Sackey
(74) *Attorney, Agent, or Firm*—Luedeka, Neely & Graham, P.C.

(57) ABSTRACT

The present invention relates to acid addition salts of aripiprazole, a process for preparing said acid addition salts and their use to prepare or purify aripiprazole in the form of a free base or in the form of a pharmaceutically acceptable salt.

7 Claims, 10 Drawing Sheets

SALTS OF ARIPIPRAZOLE

Figure 1:
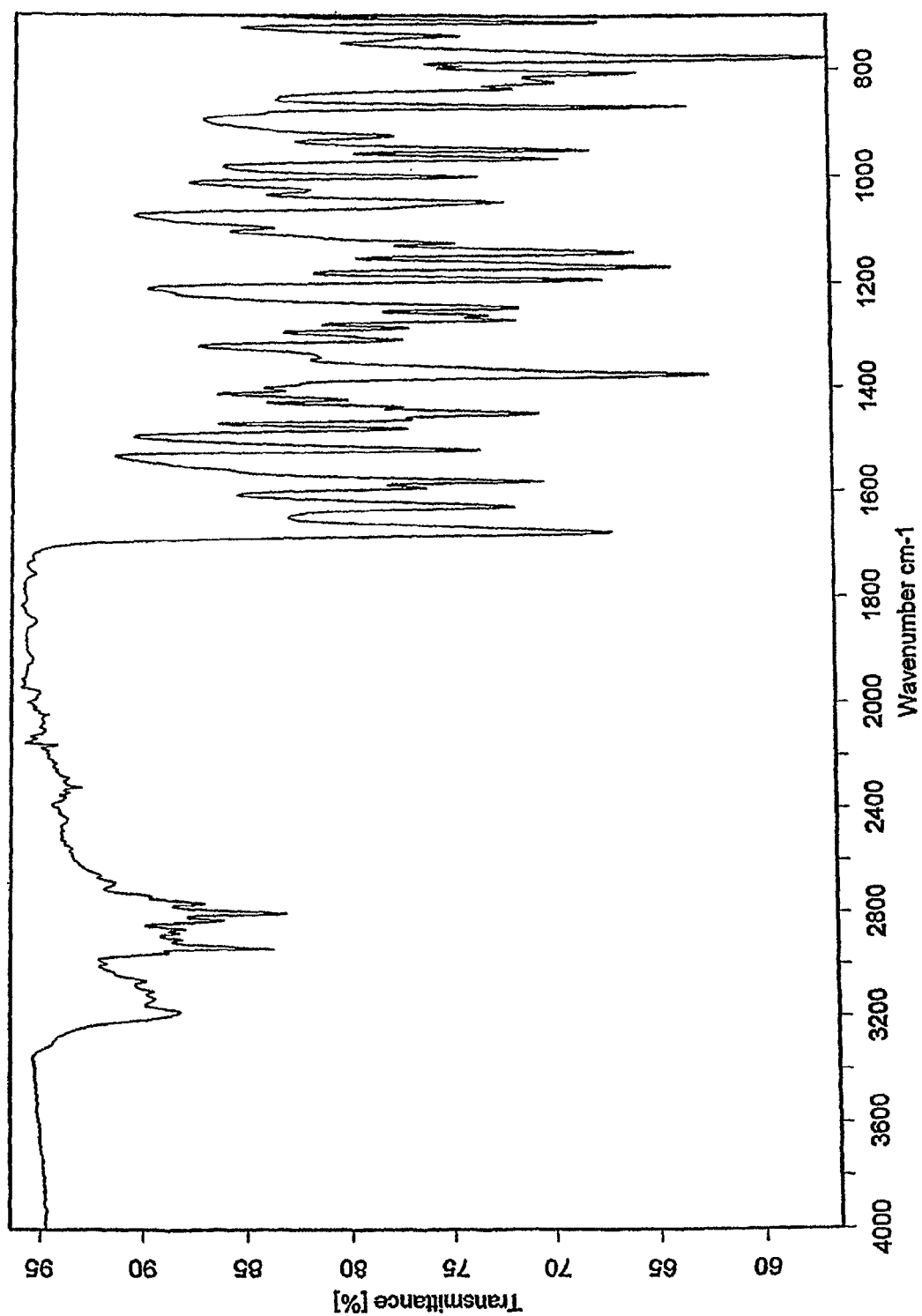
Figure 2:
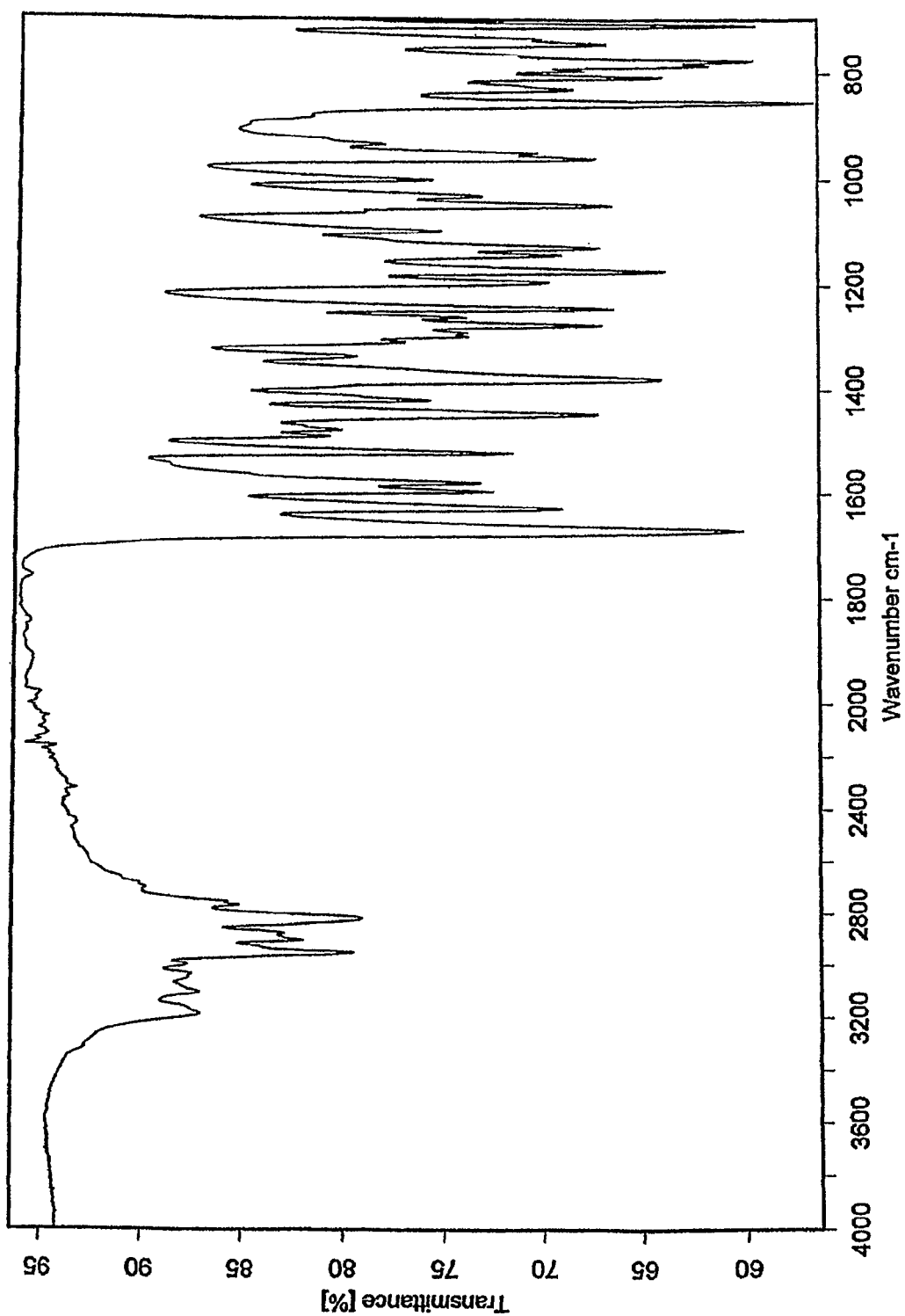
Figure 3:
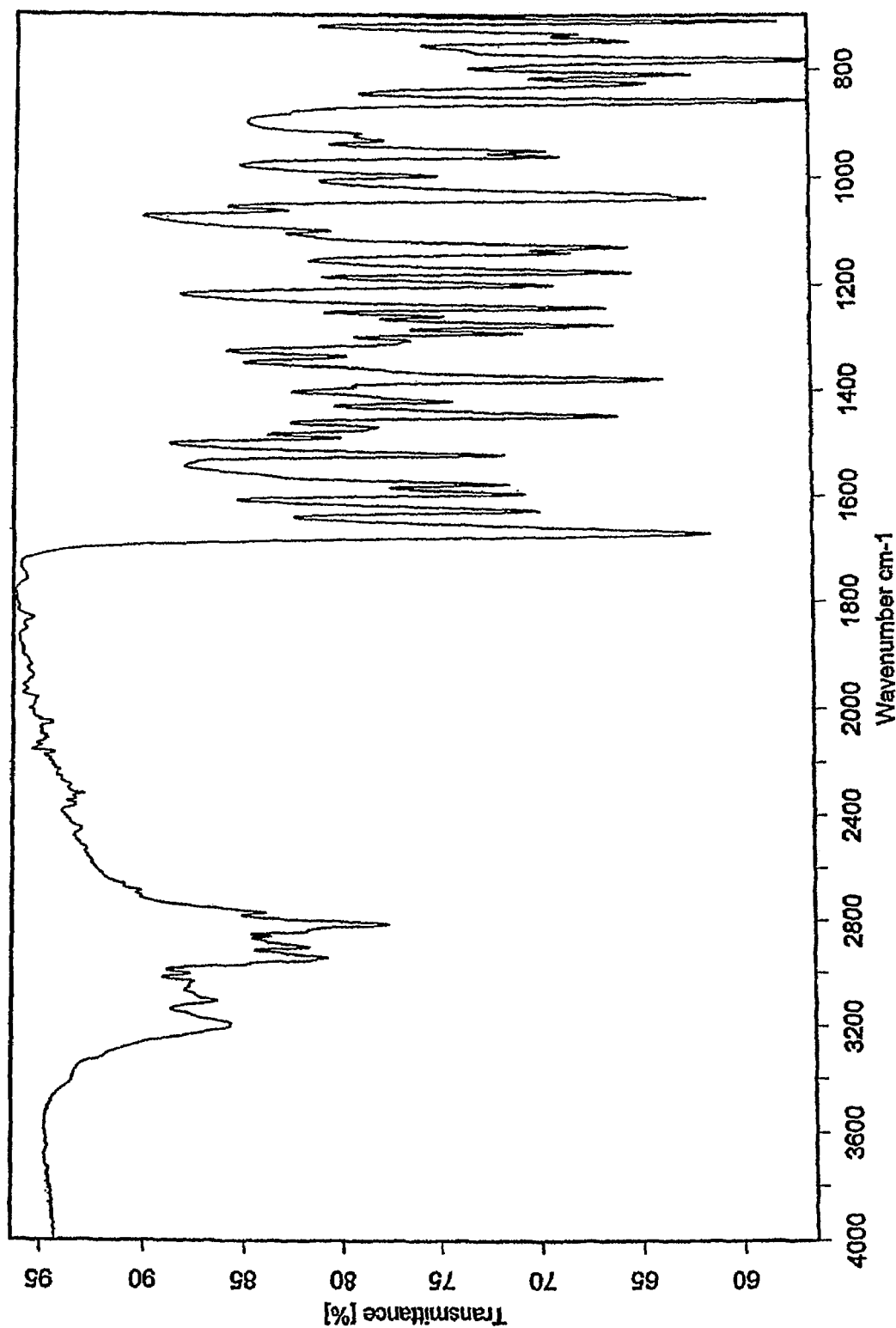
Figure 4:
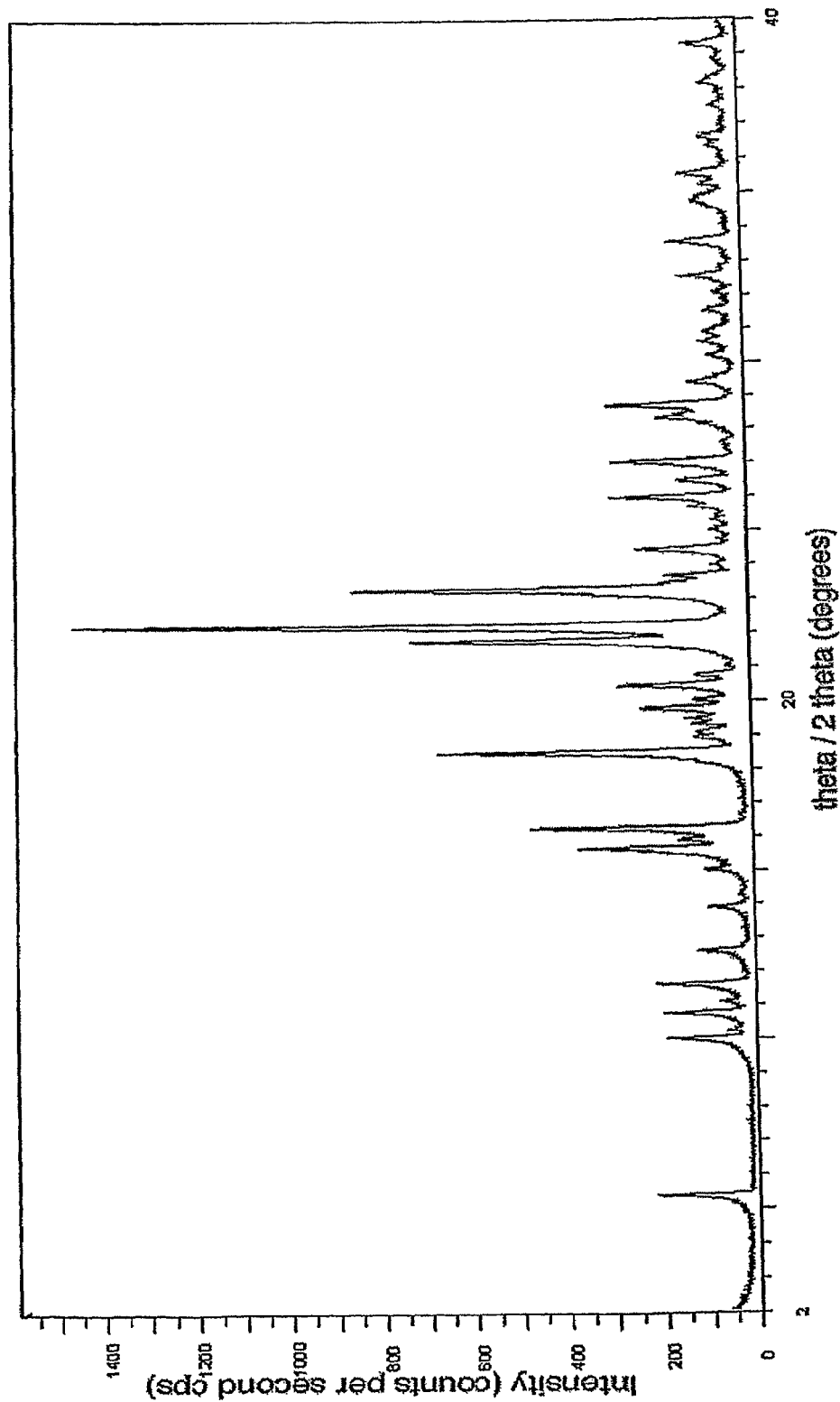
Figure 5:
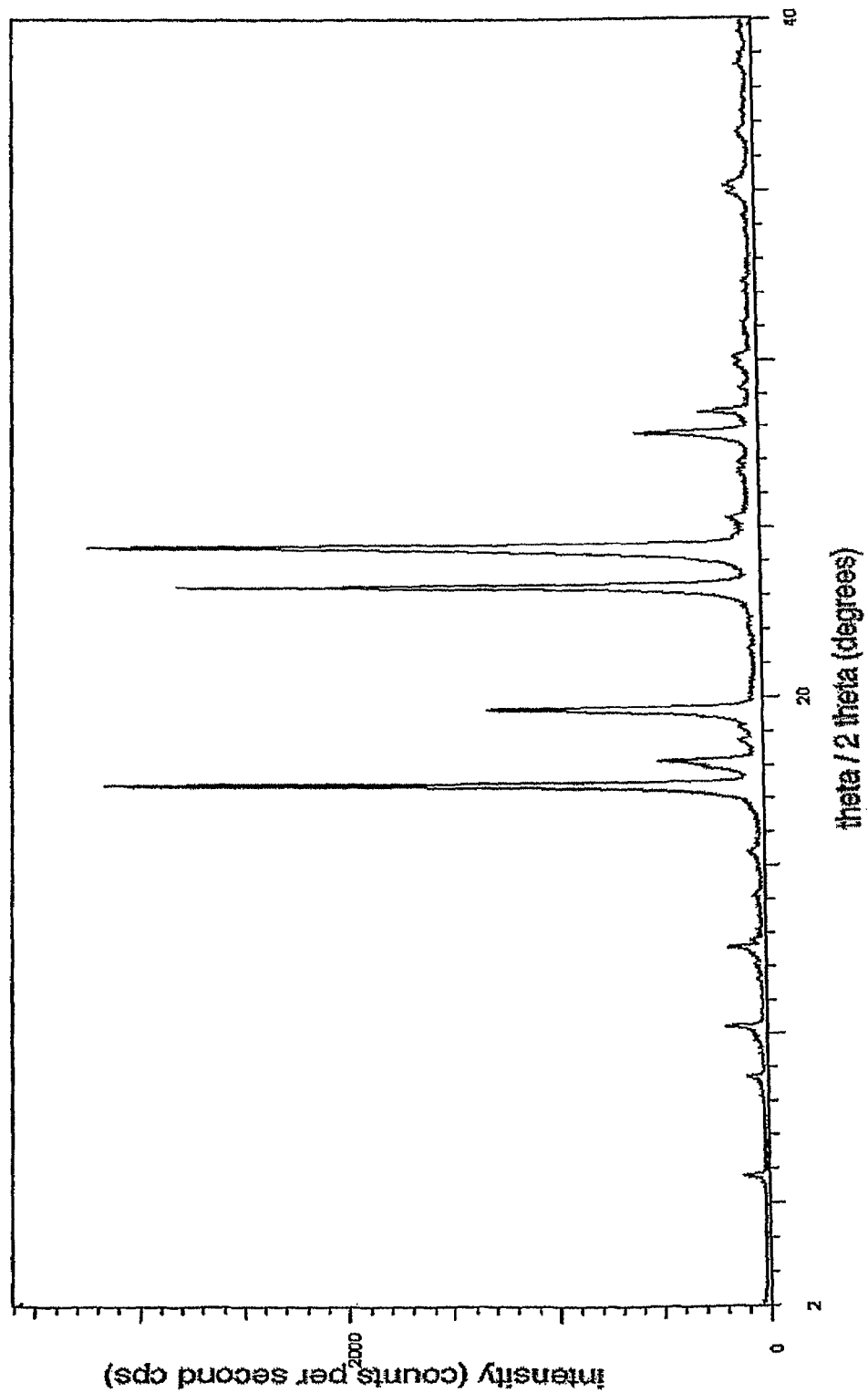
Figure 6:
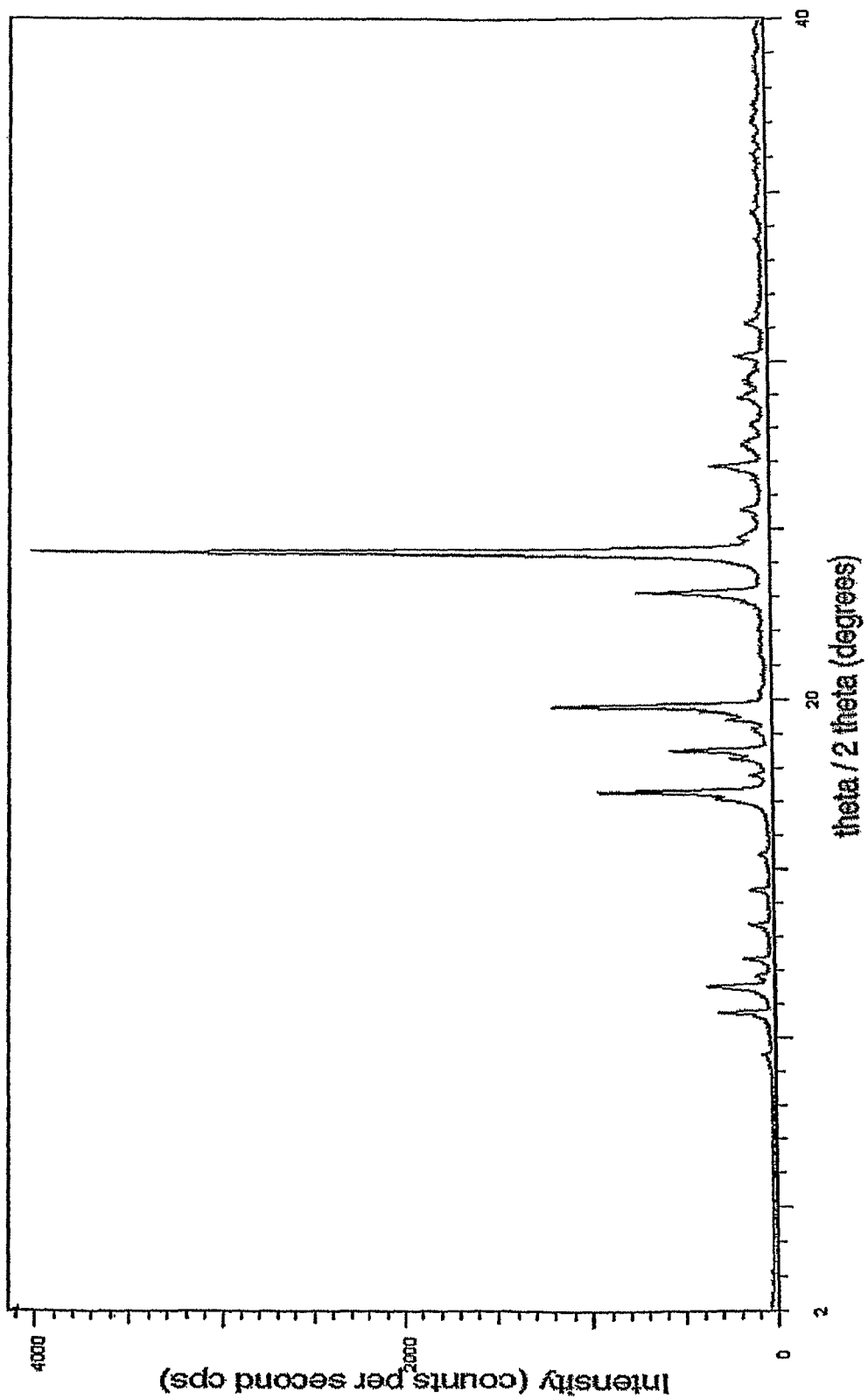
Figure 7:
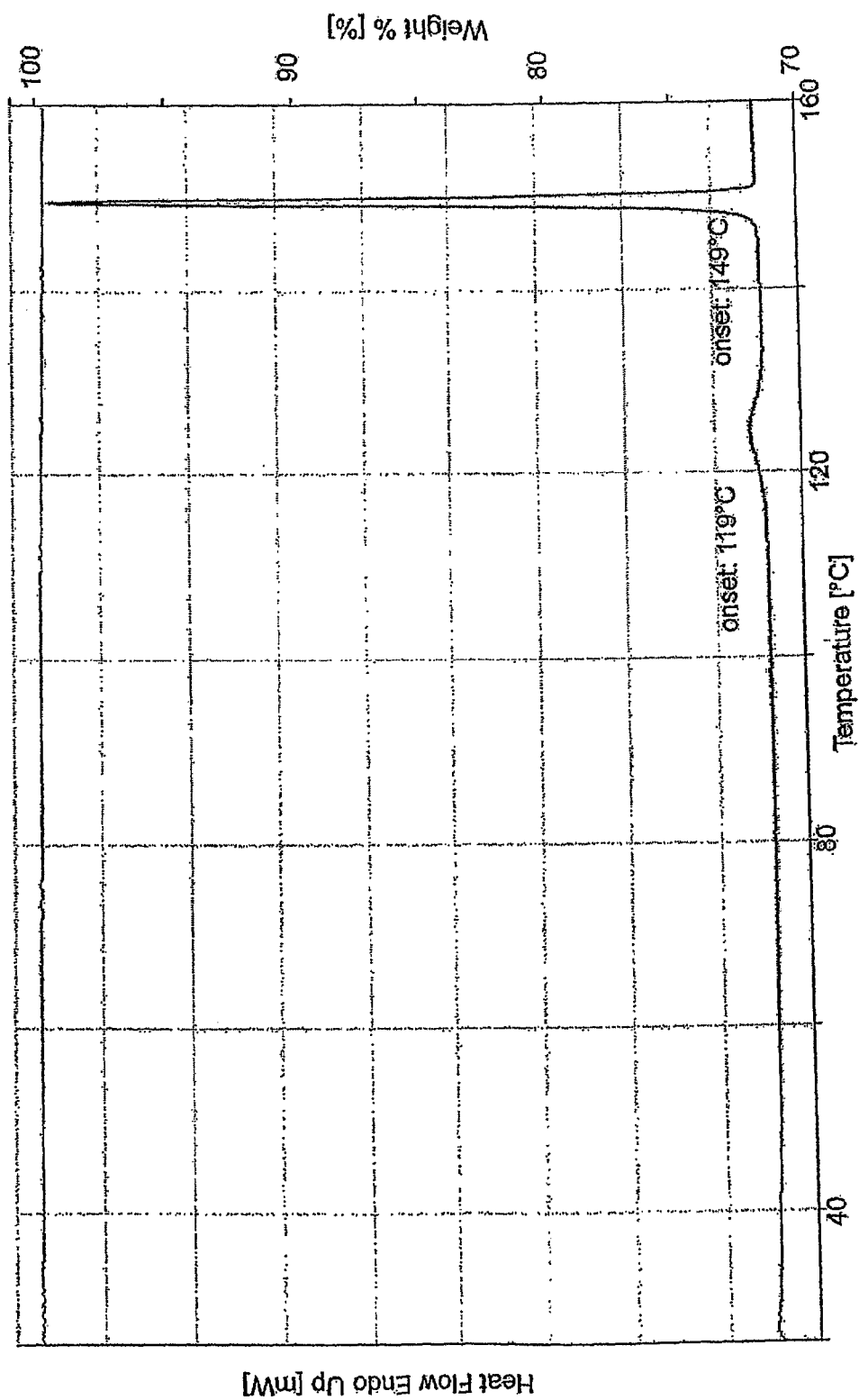
Figure 8:
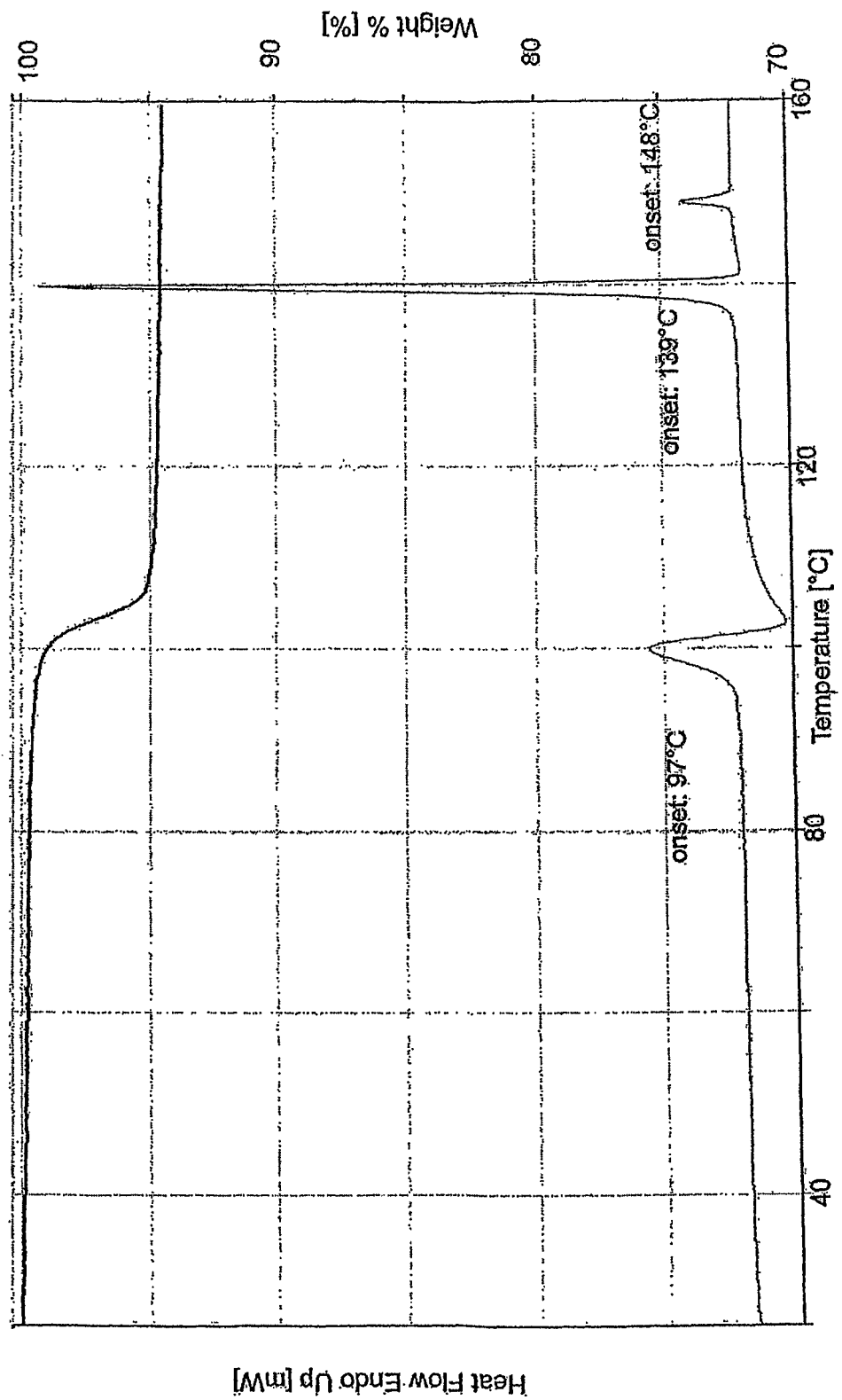
Figure 9:
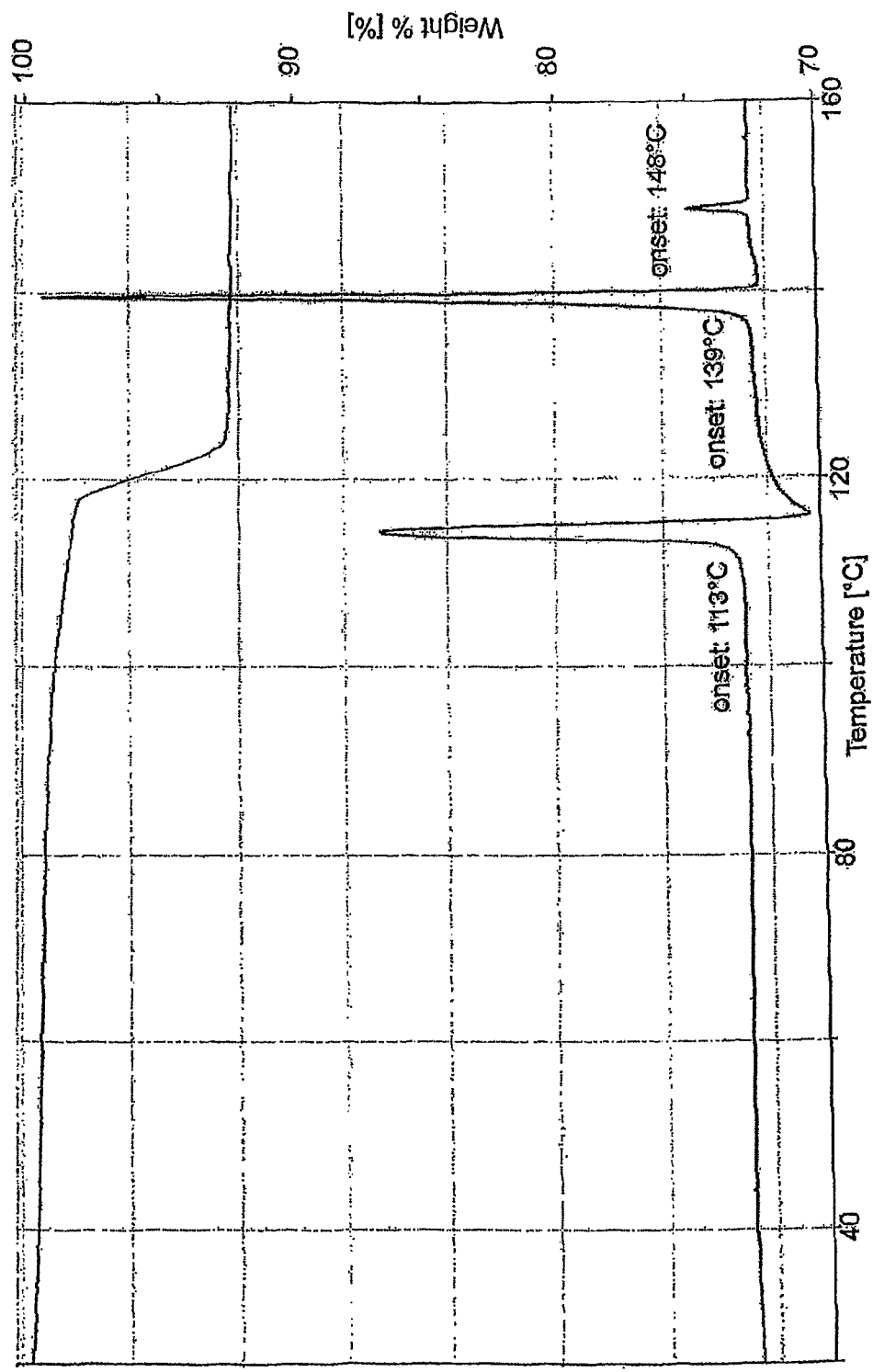
Figure 10:
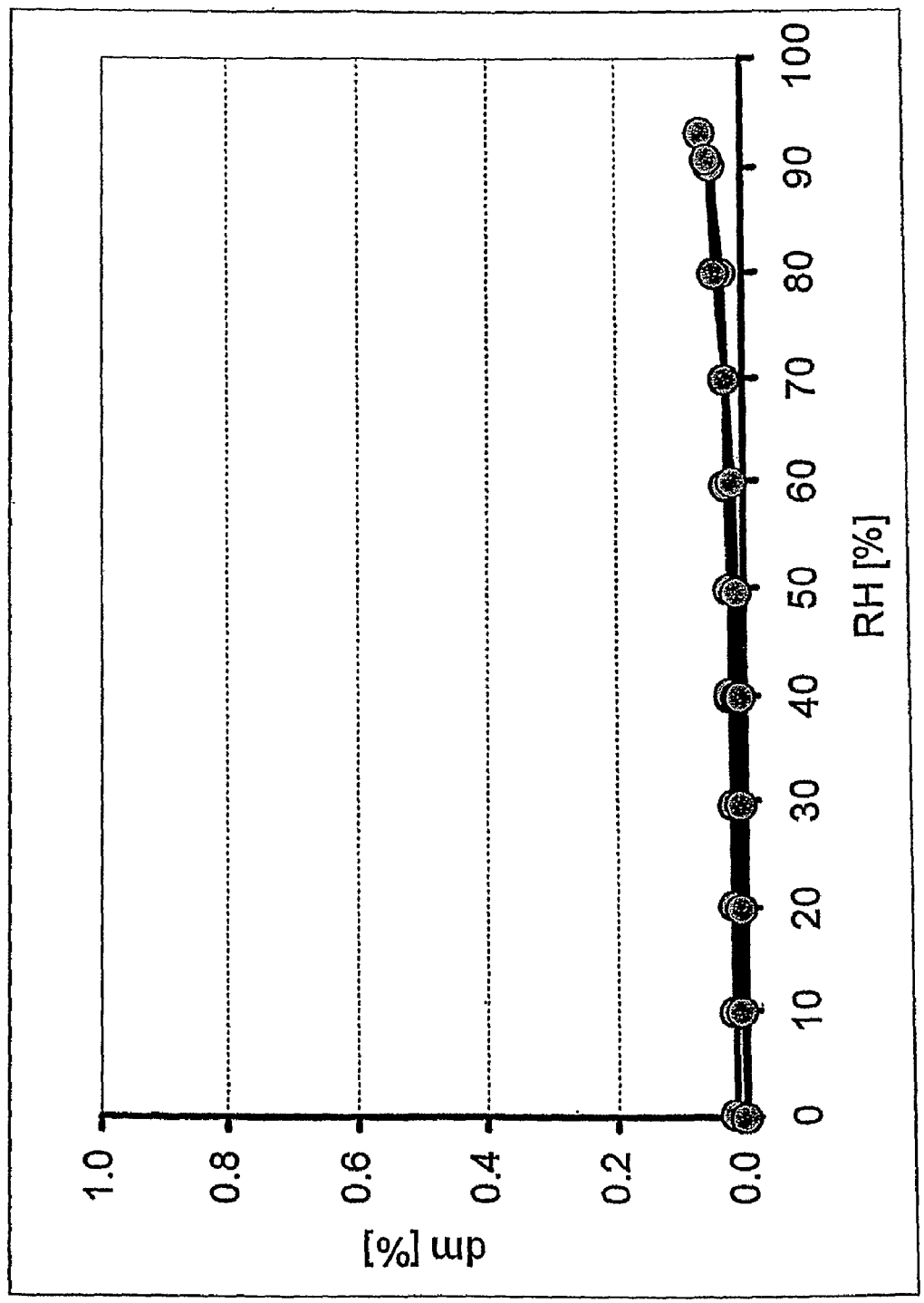

This application is the National Stage of International Application No. PCT/EP06/000726, filed on Jan. 27, 2006. This application also claims the benefit under 35 U.S.C. §119(a) of the earlier filing dates of both European Patent Application No. 05001638.5 filed on Jan. 27, 2005, and European Patent Application No. 05001639.3 filed on Jan. 27, 2005.

The present invention relates to novel acid addition salts of aripiprazole, a process for preparing said novel acid addition salts and their use to prepare aripiprazole in the form of a free base or in the form of a pharmaceutically acceptable salt.

The compound 7-{4-[4-(2,3-dichlorophenyl)-1-piperazinyl]butoxy}-3,4-dihydro-2(1H)-quinolinone and its pharmaceutical acceptable salts are known under the INN aripiprazole to be useful in treating mental disorders such as schizophrenia (see for example Merck Index, 13$^{th}$ edition, item no. 791).

A process for the preparation of aripiprazole or pharmaceutical acceptable salts thereof has been disclosed, e.g. in EP-A-367141, to involve the reaction of a carbostyril compound represented by formula

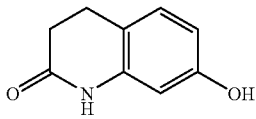

II with a compound of formula

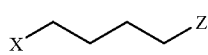

III wherein X and Z are the same or are different and each denote a halogen atom, or a group which is similarly to halogen groups suitable to undergo a substitution reaction, to result in a carbostyril derivative of formula

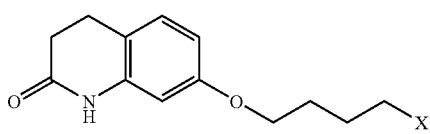

IV which is then further reacted with a piperazine compound of formula

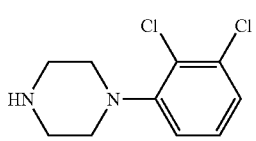

V to give aripiprazole of formula

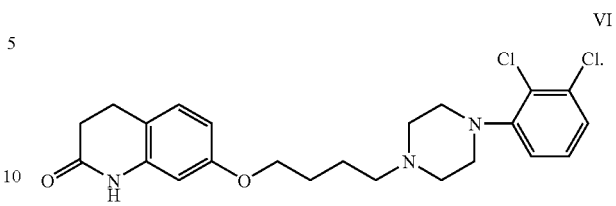

VI

The reaction of a compound of formula II with a compound of formula III does not yield in pure compound IV because of substantial amounts of side-products which result from substitution reactions other than the desired main reaction. In particular, the formation of a dimeric impurity of formula

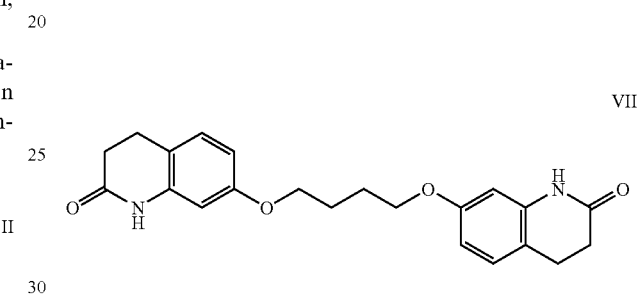

VII may usually be observed in substantial amounts. A dimeric impurity of formula VII is difficult to remove from the desired end product aripiprazole or from an intermediate compound of formula IV. For example a purification of a compound of formula IV is disclosed in EP-A-367141 by means of chromatography on silica gel which is known to be slow and expensive and thus difficult to apply in industrial scale. Consequently, there is a need for an improved process by which aripiprazole could be prepared and purified more easily from impurities such as a compound of formula VII.

The present invention provides therefore a process for preparing aripiprazole or a pharmaceutically acceptable salt thereof in high yield and high purity via acid addition salts of aripiprazole. The process of the present invention is easily applicable and is able to be scaled up easily, e.g. to an industrial scale.

The present invention provides in one aspect a process for the production of aripiprazole or a pharmaceutically acceptable salt thereof comprising the steps of preparing and isolating an acid addition salt of aripiprazole or a solvate thereof and converting the obtained acid addition salt or solvate thereof into aripiprazole in free form. Optionally, aripiprazole in free form may be converted into a pharmaceutically acceptable salt of aripiprazole. Pharmaceutically acceptable salts of aripiprazole include those salts mentioned in EP-A-367141 such as alkali- or earth alkaline metal salts, e.g. sodium, potassium, calcium or magnesium salt of aripiprazole.

Suitable acid addition salts of aripiprazole are those of formula VIII as defined below, e.g. those of formula I as defined below.

A process for the production of aripiprazole according to the present invention may comprise the steps of a) reacting a compound of formula

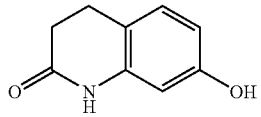

with a compound of formula

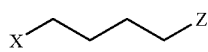

wherein X and Z are the same or different and each denote a halogen atom, or a group which is similarly to halogen groups suitable to undergo a substitution reaction such as a lower alkanesulfonyloxy-, e.g. a $(C_{1-4})$alkanesulfonyloxy-group, an arylsulfoxy- or an aralkylsulfonyloxy-group, to obtain a compound of formula

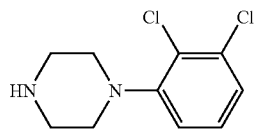

wherein X denotes as in formula III, b) reacting a compound of formula IV as obtained from step a) with a compound of formula

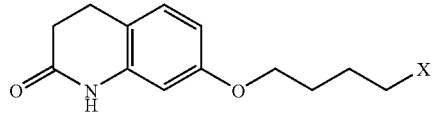

to obtain a compound of formula

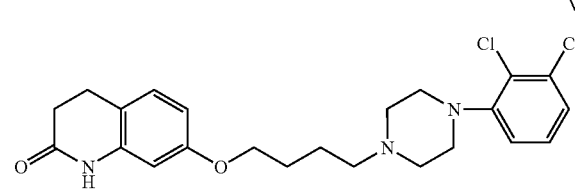

c) isolating the compound of formula VI as obtained in step b) in the form of an acid addition salt of formula

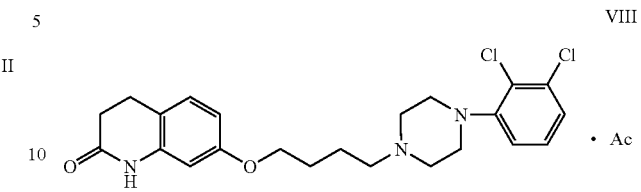

or a solvate thereof, wherein Ac is an organic or anorganic acid, and d) converting an acid addition salt of formula VIII as obtained from step c) into a compound of formula VI to isolate aripiprazole in free form which may optionally be further converted into a pharmaceutically acceptable salt of aripiprazole.

If not otherwise indicated herein, any alkyl group includes $(C_{1-8})$alkyl such as $C_{(1-6)}$alkyl, for example lower alkyl. Lower alkyl or lower alkane includes $(C_{1-4})$alkyl or $(C_{1-4})$ alkane respectively, such as methyl, ethyl, n-propyl, isopropyl or butyl. Similarly, lower alkanol includes $(C_{1-4})$alkanol such as ethanol, iso-propanol or tert.-butanol. Halogen includes a fluoro-, bromo-, chloro- and a iodo-group, preferably a bromo- or a chloro-group, more preferably a chloro group. Any aryl includes substituted or unsbstituted $(C_{6-18})$ aryl, e.g. phenyl or naphtyl. Aralkyl includes an aryl group as defined above linked to an alkyl group as defined above.

Step a), i.e. the reaction of a compound of formula II with a compound of formula III may be carried out according to methods known in the art, e.g. under conditions known for such type of reaction, for instance as described in EP-A-367141.

Reaction step b), i.e. the alkylation reaction of a compound of formula IV with a compound of formula V may be carried out in analogy, e.g. according to methods known in the art, for example as disclosed in EP-A-367141 or in EP-A-226441. However, preferably, a compound of formula IV is reacted with a compound of formula V without prior purification. For example the alkylation process of step b) may be performed under anhydrous conditions in presence of a base, e.g. a tert. or secondary amine or an alkali or earth alkali carbonate or hydrogencarbonate, e.g. sodium or potassium carbonate or sodium or potassium hydrogencarbonate. The alkylation is also conveniently performed in presence of a protic solvent, e.g. water or a lower alkanol in presence of an alkali or earth alkali carbonate. In a preferred embodiment X in compounds of formula IV represents bromine, iodine or chlorine. Iodine may be introduced into compounds of formula IV by adding a iodine source e.g. NaI or a quaternary ammonium iodide to a compound of formula IV wherein X represent a halogen different from iodine e.g. chlorine or bromine.

The compound of formula VI as obtained from step b) is either isolated or, preferably, is not isolated from the reaction mixture of step b) before step c) is carried out. For example, a compound of formula VI as obtained in step b) may be extracted from an aqueous reaction mixture into an inert organic solvent as defined below and salt formation of step c) is performed as described below under step c).

An optional isolation of a compound of formula VI from a reaction mixture of step b) may be carried out according to known methods, e.g. by filtration.

The preparation of an acid addition salt of formula I in step c) may be carried out by adding a suitable anorganic or organic acid to a suspension or solution of a compound of formula VI as obtained from step b) in an inert solvent. Suitable anorganic or organic acids are acids which are able to form acid addition salts with aripiprazole and which do not react with other parts of the aripiprazole molecule. Particularly, suitable acids include hydrochloric acid, hydrobromic acid, hydroiodic acid, fumaric acid, sulfuric acid, oxalic acid, phenylphosphonic acid, maleic acid, tartaric acid, citric acid, malic acid, mesitylenesulphonic acid, benzoic acid and tetrafluoroboric acid. Preferably, Ac denotes hydroiodic acid, hydrobromic acid, mesitylenesulphonic acid, oxalic acid, mesitylenesulphonic acid, tetrafluoroboric acid, phosphoric acid or phenylphosphonic acid. In one more preferred embodiment Ac denotes oxalic acid. In another more preferred embodiment Ac denotes hydroiodic acid, hydrobromic acid, mesitylenesulphonic acid, tetrafluoroboric acid or phenylphosphonic acid. Suitable inert solvents include lower alkanols, esters, nitriles, e.g. ($C_{2-4}$)alkylnitrile such as acetonitrile, halogenated solvents, ketones or ethers or mixtures thereof. Lower alkanols include ($C_{1-4}$) alkanols such as methanol, ethanol, isopropanol or butanols. Esters include ($C_{1-4}$)alkanoic acid ($C_{1-4}$)alkyl esters, e.g. acetic acid ($C_{1-4}$) alkyl esters such as ethylacetate or n-butylacetate. Halogenated hydrocarbons include chlorinated alkanes such as dichloromethane. Ethers include cyclic and acyclic ethers. Acyclic ethers are symmetric or asymmetric lower alkyl-lower alkyl ethers, e.g. ($C_{1-4}$)alkyl-($C_{1-4}$)alkylether, such as diethylether whereas cyclic ethers include 5 to 6 membered ($C_{3-5}$)cycloalkyl- or ($C_{3-5}$)cycloalkenyl-ethers, such as tetrahydrofuran, dioxan or trioxan.

The ratio of the amounts of aripiprazole and the corresponding acid in the salt formation process is not critical. The molar ratio of the corresponding acid to aripiprazole may for example be 1 to 3, such as 1 to 2, e.g. 1.1 to 2 molar equivalents of the corresponding acid. The reaction temperature during the salt formation reaction is not critical but should be below the boiling point of the used solvent under the reaction conditions. The salt formation may be performed from $-50°$ C. to $100°$ C., e.g from $0°$ C. to $50°$ C., for example at room temperature.

The acid addition salt may be isolated in conventional manner, e.g. by filtration and is then dried by conventional methods such as vacuum drying.

The acid addition salts of aripiprazole of formula VIII may be prepared from isolated compounds of formula VI or from reaction mixtures of compound of formula VI with compounds of formula IV and of formula V.

Step d) consisting of the conversion of an acid addition salt of aripiprazole or a solvate thereof into aripiprazole of formula VI in free form may be carried out by dissolving or suspending the acid addition salt of formula VIII as obtained from step c) in an appropriate solvent. Appropriate solvents may be identified by skilled persons in routine tests and include water, a mixture of water with a protic solvent, e.g. a lower alkanol, or an organic solvent which is not mixable with water or which is only partly soluble in water, e.g. dichloromethane, in particular polar organic solvents, e.g. amides such as N,N-dimethylacetamide or N,N-dimethylformamide, or e.g. dimethylsulfoxide or sulfolane.

The pH value is then adjusted to a basic pH value, e.g. above a pH value corresponding to the pKs value of a compound of formula VI in free base form, measured under the reaction conditions, for example to a pH value of above pH 7.0 such as above pH 7.5, in particular to a pH from pH 8 to pH 13 such as about pH 9, by addition of a base. A suitable base may be for example a tertiary amine, e.g. a tri-(lower alkyl) amine, an alkali or earth alkaline metal hydroxide, e.g. NaOH or KOH or an alkali or earth alkaline carbonate e.g. sodium carbonate or potassium carbonate.

After the pH value is adjusted to a basic pH value, either i) aripiprazole optionally in form of a solvate, e.g. as a hydrate, may precipitate and may be isolated e.g. by conventional methods such as filtration from the reaction mixture; or ii) a countersolvent may be added to the reaction mixture to complete or induce crystallization of aripiprazole in free form or in the form of a solvate, followed by isolation by conventional methods, e.g. filtration; or iii) an organic extraction solvent may be added which forms a separate phase under the reaction conditions in order to extract a compound of formula VI in free form. Suitable organic extraction solvents include for instance halogenated hydrocarbons such as halogenated lower alkanes, e.g. dichloromethane, esters, such as ($C_{1-4}$) alkanoic acid ($C_{1-8}$)alkyl esters, e.g. ethylacetate, or ketones such as ($C_{5-8}$)ketones, e.g. methylisobutylketone, or mixtures of those solvents. Aripiprazole may then be precipitated and isolated from the organic extraction solvent or from the organic extraction solvent mixture, preferably after separation of the two phases, in conventional manner, e.g. by adding a counter-solvent, evaporating the organic solvent and/or cooling to decrease the temperature, in order to initiate and accelerate precipitation followed by e.g. filtering the precipitate. The extraction solvent may be already present during the step of adjusting the pH value to a basic pH.

Suitable countersolvents in the isolation steps of aripiprazole are solvents that decrease the solubility of the free form of a compound of formula VI in the solvent in which the compound of formula VI is dissolved. Suitable countersolvents may be identified by a skilled persons by routine tests and include for instance lower alkanols, e.g. methanol or ethanol, nitriles, e.g. acetonitrile, ethers, e.g. methyl tert. butylether, ketones, e.g. ($C_{3-8}$)-ketones such as acetone or methylisobutylketone or esters, e.g. ($C_{1-4}$)-alkanoic acid ($C_{1-4}$)-alkyl esters such as ethylacetate, optionally in the presence of water.

In a process of the present invention aripiprazole may be precipitated in free, e.g. non-solvated form, or in the form of a solvate if the solvent with which aripiprazole forms a solvate is present during precipitation. If for example aripiprazole is precipitated in one of the above mentioned alternatives of step d) in the presence of methanol or ethanol then aripiprazole may usually be isolated in the form of a solvate with methanol or ethanol, respectively. If for example aripiprazole is precipitated from water optionally in the presence of an organic solvent, e.g. an alcohol, e.g. ethanol, e.g. about 80% (v/v EtOH/$H_2O$) water, aripiprazole in form of its hydrate is obtained. The hydrate of aripiprazole may be converted to other forms of aripiprazole by known methods.

If for example aripiprazole is precipitated in one of the above mentioned alternatives of step d) in the presence of isopropanol, form X of aripiprazole is obtained. Form X of aripiprazole is characterized by an X-ray powder diffraction diagram with peaks at 10.0, 11.6, 15.7, 16.3, 18.5, 20.4, 21.8, 22.2, and 23.3 degrees Θ. In a preferred embodiment of the process described above, the aripiprazole isolated in free form is an aripiprazole which is substantially pure in terms of crystalline form, e.g. form X, by using appropriate seed crystals and containing less than 0.1%, preferably 0.05% (w/w) of a compound of formula VII. According to this process, the aripiprazole form X is a pure crystalline form containing less than 5%, preferably 1%, of other crystalline or polymorphic forms.

Optionally, aripiprazole of formula VI in free form as obtained from a process of the present invention is converted into a pharmaceutically acceptable salt of aripiprazole according to known methods, e.g. according to the teaching of EP-A-367141.

Aripiprazole in free form or in the form of a pharmaceutically acceptable salt prepared by a process according to the present invention may be isolated in high purity, in particular with low levels of impurities such as the dimeric impurity of formula VII as defined above. A process of the present invention may thus result in aripiprazole in free form or in the form of a pharmaceutically acceptable salt with less than 0.1% (w/w) of a compound of formula VII as defined above, for instance from 0.02 to 0.05% (w/w), e.g. less than 0.05% (w/w). The content of a compound of formula VII in aripiprazole in free form or in the form of a pharmaceutically acceptable salt can be determined by HPLC.

A further advantage of the processes of the present invention by preparing acid addition salt of formula VIII in the preparation of aripiprazole is that crude compound of formula IV, being e.g. obtained from reaction of a compound of formula II with a compound of formula III, may be reacted with a compound of formula V without a prior purification step such as chromatography.

Some of the acid addition salts which may be used in a purification process of aripiprazole of the present invention are novel.

Therefore, the present invention relates in a further aspect to an acid addition salt of formula

I

· Ad wherein Ad denotes hydroiodic acid, hydrobromic acid, oxalic acid, mesitylenesulphonic acid, tetrafluoroboric acid, phosphoric acid or phenylphosphonic acid, or a solvate thereof. The acid addition salts may exist in amorphous or in crystalline form, e.g. in crystalline form. A solvate includes a solvate with an organic compound, e.g. an inert solvent used for the formation of the acid addition salt as mentioned below, as well as a hydrate. In one preferred embodiment Ad denotes hydroiodic acid, hydrobromic acid, mesitylenesulphonic acid, tetrafluoroboric acid or phenylphosphonic acid. In another preferred embodiment Ad denotes oxalic acid.

An acid addition salt of formula I as defined above may be prepared by combining aripiprazole and a corresponding acid, e.g. by adding the corresponding acid to a solution or suspension of aripiprazole in an inert solvent, or by adding a solution or suspension of aripiprazole in an inert solvent to the corresponding acid.

Thus, the present invention provides in a further aspect a process for preparing an acid addition salt of formula I as defined above or a solvate thereof by reacting aripiprazole with an acid as defined above in formula I by Ad in an inert solvent.

The ratio of the amounts of aripiprazole and the corresponding acid in the salt formation process is not critical. The molar ratio of the corresponding acid to aripiprazole may for example be 1 to 3, such as 1 to 2, e.g. 1.1 to 2 molar equivalents of the corresponding acid.

Suitable inert solvents for the salt formation process are lower alkanols, esters, nitriles, e.g. $(C_{2-4})$alkylnitrile such as acetonitrile, halogenated solvents, ketones or ethers or mixtures thereof. Lower alkanols include $(C_{1-4})$ alkanols such as methanol, ethanol, isopropanol or butanols. Esters include $(C_{1-4})$alkanoic acid $(C_{1-4})$alkyl esters, e.g. acetic acid $(C_{1-4})$ alkyl esters such as ethylacetate or n-butylacetate. Halogenated hydrocarbons include chlorinated alkanes such as dichloromethane. Ethers include cyclic and acyclic ethers. Acyclic ethers are symmetric or asymmetric lower alkyl-lower alkyl ethers, e.g. $(C_{1-4})$alkyl-$(C_{1-4})$alkylether, such as diethylether whereas cyclic ethers include 5 to 6 membered $(C_{3-5})$cycloalkyl- or $(C_{3-5})$cycloalkenyl-ethers, such as tetrahydrofuran, dioxan or trioxan.

The reaction temperature during the salt formation reaction is not critical but should be below the boiling point of the used solvent under the reaction conditions. The salt formation may be performed from −50° C. to 100° C., e.g from 0° C. to 50° C., for example at room temperature. The acid addition salt may be isolated in conventional manner, e.g. by filtration and is then dried by conventional methods such as vacuum drying.

The novel acid addition salts of aripiprazole according to the present invention allow in an efficient manner the preparation of aripiprazole in sufficient purity, i.e. with a low content of impurities, particularly the dimeric impurity compound of formula VI as defined above.

A process of the present invention and the novel acid addition salts of formula I may also be used to purify aripiprazole that may have been obtained from other production processes as those via a compound of formula IV as described above. Thus, the present invention provides in another aspect a process for the purification of aripiprazole by preparing an acid addition salt of formula VIII as defined above, e.g. of formula I as defined above, isolating the acid addition salt and converting it into aripiprazole in free form.

As indicated above acid addition salts of formula VIII, particularly those of formula I are useful in the preparation and purification of aripiprazole. Hence, in a further aspect the present invention relates to the use of an acid addition salt of formula VIII, e.g. an acid addition salt of formula I, in the preparation of aripiprazole, e.g. by purifying aripiprazole in free form, in particular by depleting aripiprazole in free form from impurities such as a compound of formula VII.

The following Examples will illustrate the present invention but are not intended to limit the present invention in any way. All temperatures are given in degree Celsius and are uncorrected.

ABBREVIATIONS

APZ=Aripiprazole
Mp=melting point
DCP=dichlorophenylpiperazine
BrDCS=7-(4-bromomethoxy)-3,4-dihydro-2(1H)-quinolinone
ClDCS=7-(4-chloromethoxy)-3,4-dihydro-2(1H)-quinolinone
THF=tetrahydrofuran
DMAC=N,N-dimethylacetamide
DIPA=diisopropylamine
MED=dichloromethane

EXAMPLE 1

Aripiprazole Oxalate

To a solution of 1.00 g APZ in 25 ml THF is added a solution of 0.20 g oxalic acid in 0.5 ml THF. After 1 minute stirring at 25° C. crystallization starts. The suspension is stirred for one hour at 25° C. and then stirring is continued for one hour in an ice bath. The obtained product is then isolated by filtration. The product is washed with 10 ml of THF and drying is performed for 15 hours at 50° C. in vacuo.

| Yield: | 1.05 g crystalline powder |
|---|---|
| Mp: | 195-202° C. |
| Aripiprazole: | 81.3% |
| Oxalic acid: | 15.8% |
| THF: | 1.7% |

EXAMPLE 2

Aripiprazole oxalate

To a solution of 1.00 g APZ in 25 ml methylenechloride is added a solution of 0.20 g oxalic acid in 0.5 ml ethanol. After 2 minutes stirring at 25° C. crystallization starts. The suspension is stirred for one hour at 25° C. and then stirring is continued for one hour in an ice bath. The product is then isolated by filtration. The product is washed with 10 ml of methylenchloride and drying is performed for 15 hours at 50° C. in vacuo.

| Yield: | 1.00 g crystalline powder |
|---|---|
| Mp: | 202° C. |
| Aripiprazole: | 80.7% |
| Oxalic acid: | 15.1% |
| MED: | 4.1% |
| Ethanol: | 0.3% |

EXAMPLE 3

Aripiprazole Mesitylenesulfonate

To a solution of 1.00 g APZ in 25 ml THF is added a solution of 0.39 g mesitylenesulfonic acid dehydrate in 0.5 ml THF. The suspension formed is stirred for one at 25° C. and then stirring is continued for one hour in an ice bath. Then the product is isolated by filtration. The product is washed with 10 ml of THF and drying is performed for 15 hours at 60° C. in vacuo.

| Yield: | 0.90 g crystalline powder |
|---|---|
| Mp: | 216° C. |
| Aripiprazole: | 68.7% |
| Mesitylenesulfonic acid: | 29.7% |

EXAMPLE 4

Aripiprazole Mesitylenesulfonate

To a solution of 1.00 g APZ in 25 ml methylenechloride is added a solution of 0.39 g mesitylenesulfonic acid dehydrate. The suspension formed is stirred for one at 25° C. and then stirring is continued for one hour in an ice bath. The product is then isolated by filtration. The product is washed with 10 ml of methylenechloride and drying is performed for 15 hours at 60° C. in vacuo.

| Yield: | 1.090 g crystalline powder |
|---|---|
| Mp: | 216° C. |
| Aripiprazole: | 69.1% |
| Mesitylenesulfonic acid: | 31.1% |

EXAMPLE 5

Aripiprazole Toluenesulfonate

To a solution of 1.00 g APZ in 25 ml THF is added a solution of 0.28 g p-toluenesulfonic acid monohydrate in 0.5 ml THF. The suspension formed is stirred for one hour at 25° C. and then stirring is continued for one hour in an ice bath. The product is then isolated by filtration. The product is washed with 10 ml of THF and drying is performed for 15 hours at 60° C. in vacuo.

| Yield: | 0.90 g crystalline powder |
|---|---|
| Mp: | 158° C. |
| Aripiprazole: | 72.9% |
| Toluenesulfonic acid: | 27.4% |

EXAMPLE 6

Aripiprazole Phosphate

A solution of 1.00 g APZ in 25 ml methylenechloride is warmed to 35° C. and then dropwise 0.44 g phosphoric acid 85% are added. The suspension formed is stirred for one hour at 35° C. and then stirring is continued for one two hour at 25° C. The product is then isolated by filtration. The product is washed with 10 ml of methylenechloride and drying is performed for 15 hours at 60° C. in vacuo.

| Yield: | 1.39 g crystalline powder |
|---|---|
| Mp: | 176° C. |
| Aripiprazole: | 65.2% |

EXAMPLE 7

Aripiprazole Phosphate

A solution of 1.00 g APZ in 25 ml methylenechloride is warmed to 35° C. and then a solution of 0.44 g phosphoric acid (85%) in 1 ml Methanol is added dropwise. The suspension formed is stirred for one hour at 25° C. and then stirring is continued for two hours at 0° C. The product is then isolated by filtration. The product is washed with 10 ml of methylenechloride and drying is performed for 15 hours at 60° C. in vacuo.

| Yield: | 1.28 g crystalline powder |
|---|---|
| Mp: | 179° C. |
| Aripiprazole: | 70.3% |

EXAMPLE 8

Aripiprazole Hydroiodide

To a solution of 1.00 g APZ in 25 ml THF is added a solution of 0.76 g hydroiodic acid (58%). The formed suspension is stirred for one hour at 25° C. and then stirring is continued for one hour in an ice bath. The product is then isolated by filtration. The product is washed with 10 ml of THF and drying is performed for 15 hours at 60° C. in vacuo.

| | |
|---|---|
| Yield: | 0.94 g crystalline powder |
| Mp: | 224° C. |
| Aripiprazole: | 74.8% |
| Hydroiodic acid: | 25.0% |

EXAMPLE 9

Aripiprazole Tetrafluoroborate

To a solution of 1.00 g APZ in 25 ml THF is added a solution of 0.29 g tetrafluoroboric acid The suspension formed is stirred for one at 25° C. and then stirring is continued for one hour in an ice bath. The product is then isolated by filtration. The product is washed with 10 ml of THF and drying is performed for 15 hours at 60° C. in vacuo.

| | |
|---|---|
| Yield: | 0.81 g crystalline powder |
| Mp: | 190° C. |
| Aripiprazole: | 72.6% |

EXAMPLE 10

Aripiprazole Phenylphosphonate

To a solution 1.00 g APZ in 25 ml methylenechloride is added a solution of 0.70 g phenylphosphonic acid. The formed suspension is stirred for one hour at 25° C. and then stirring is continued for one hour in an ice bath. The product is then isolated by filtration. The product is washed with 10 ml of THF and drying is performed for 15 hours at 60° C. in vacuo.

| | |
|---|---|
| Yield: | 1.37 g crystalline powder |
| Mp: | 180° C. |
| Aripiprazole: | 58.3% |
| Phenylphosphonic acid: | 39.9% |

EXAMPLE 11

Aripiprazole Hydrobromide

To a solution of 1.00 g APZ in 25 ml THF are added 1.09 g hydrobromic acid (33% in acetic acid). The suspension formed is stirred for one at 25° C. and then stirring is continued for one hour in an ice bath. The product is then isolated by filtration. The product is washed with 10 ml of THF and drying is performed for 15 hours at 60° C. in vacuo.

| | |
|---|---|
| Yield: | 1.17 g crystalline powder |
| Mp: | 233° C. |
| Aripiprazole: | 76.1% |

EXAMPLE 12

Aripiprazole Oxalate

A mixture of 10.00 g of BrDCS crude (Preparation according procedure given in U.S. Pat. No. 5,006,528, but without silica gel column chromatography), 7.00 g dichlorophenylpiperazine (DCP) and 3.49 g diisopropylamine is warmed to 85° C. After stirring for 4 hours at this temperature the reaction mixture is cooled to room temperature and diluted with a mixture of 320 ml methylenechloride and 125 ml water. After separating the phases to the product containing methylenechloride layer is added water and the pH is adjusted to 6.0 by addition of 1M sulfuric acid. After 5 minutes stirring the phases were separated and the organic phase was washed once more with 125 ml water at pH 6.0. Then 125 ml water was added and the pH is adjusted to 9.0 by addition of 1M sodium hydroxide. After separation of the layers the organic layer is dried with sodium carbonate. The dried methylenechloride layer is diluted with 320 ml methylenechloride and warmed to 35° C. At this temperature under stirring a solution of 7.46 g of oxalic acid in 10.5 ml of ethanol is added within 15 minutes. The resulting suspension is stirred for about 1 hour at approximately 20° C. and afterwards 1 hour at approximately 0° C.

The obtained product aripiprazole oxalate is isolated by filtration, washed with 100 ml of methylenechloride and dried for 15 hours at 50° C. in vacuo.

Yield: 15.15 g

EXAMPLE 13

Preparation of Aripiprazole Oxalate

A mixture of 30 ml of DMAC, 7.00 g of DCP and 3.49 g of DIPA are heated to approximately 85° C. To the turbid solution are added 10 g of BrDCS. The reaction mixture is kept at approximately 85° C. for 4 hours. The reaction mixture is cooled to room temperature and is added to a mixture of 320 ml of MED und 125 ml of water. The mixture is then stirred for approximately 15 minutes. The layers are separated and the organic layer is washed 3 times with each 125 ml of water adjusting the pH carefully to pH 6.0 with 1 M sulfuric acid. To the organic layer are added 125 ml of water and the pH is adjusted to pH 9 with 1 M sodium hydroxide solution. The layers are separated, the organic layer is filtered and is then dried with 10 g of sodium carbonate. The suspension is filtered, the filter cake is washed with 40 ml of MED. The filtrate is stored for 15 hours at around 4° C., filtered and diluted with 420 g of MED. The solution is heated to 35° C., seeding crystals of aripiprazole oxalate are added followed by a solution of 4.83 g of oxalic acid in 7 ml of ethanol within approximately 10 minutes. The suspension is stirred for 4 hours and aripiprazole oxalate is then isolated by filtration, washed with 200 ml of MED and dried at 60° C. in vacuo for 15 hours.

Yield: 11.1 g

EXAMPLE 14

Preparation of Aripiprazole from Aripiprazole Oxalate 10 g of aripiprazole oxalate are suspended in a mixture of 465 ml of MED und 235 ml of water. The pH of the suspension is adjusted with 4.65 g of sodium carbonate to pH 9.0. A solution is obtained. The layers are separated and the organic layer is washed with 235 ml of water. The organic layer is dried with 10 g of sodium carbonate. The suspension is filtered, the filter is washed with approximately 30 ml of MED. The solution is concentrated on a rotary evaporator (bath temperature 50° C.) in vacuo to approximately 35 g. To the residue 200 ml of ethanol are added and the suspension is heated to approximately 85° C. To the solution are added seeding crystals of aripiprazole and the suspension is allowed to cool to room temperature. The suspension is stirred for 2 hours at room temperature and is then stored for approximately 15 hours at approximately 4° C. The obtained aripiprazole crystals are isolated by filtration, washed with 150 ml of ethanol and are dried in vacuo at 60° C. for 4 hours.

Yield 7.05 g

Content of a dimer compound of formula VII as defined above: <0.05% (HPLC);

Single other impurity: <0.05%

EXAMPLE 15

Preparation of Aripiprazole from Aripiprazole Oxalate 10 g aripiprazole oxalate containing 33.5% oxalic acid are suspended in 300 ml isopropanol and heated to 50° C. under stirring. 9.8 ml 1,1,3,3-Tetramethylguanidine (2.1 equivalents) are added through a dropping funnel during 10 min. A clear solution is obtained at the end of the base addition. 0.2 g seeds of aripiprazole form X are added and after stirring for 1 hour at 50° C. the mixture is cooled down to 0° C. in one hour. After stirring for one hour the suspension is reheated to 50° C., stirred at this temperature for one or two hours, then again cooled to 0° C. After stirring for one hour at 0° C. the white crystalline precipitate is filtered, the filter cake washed with ca. 2×10 ml isopropanol and the wet product dried in vacuo at room temperature over night or at 60° C. for 3 hours to yield 5.98 g (95.5%) aripiprazole form X.

EXAMPLE 16

Preparation of Aripiprazole from Aripiprazole Oxalate

Example 15 is repeated but instead of using 1,1,3,3-Tetramethylguanidine 11.7 ml of 1,8-Diaza-7-bicyclo[5.4.0]undecene (DBU, 2.1 equivalents) as base is used. The yield is 5.95 g (95.1%) of form X of aripiprazole.

EXAMPLE 17

Preparation of Aripiprazole from Aripiprazole Oxalate a)

20 g aripiprazole oxalate containing 33.5% oxalic acid are suspended in 300 ml ethanol 80% (v/v $H_2O$) and heated to 70° C. under stirring. 24.2 ml Triethylamine (2.1 equivalents) are added through a dropping funnel during 3 min. A clear solution is obtained at the end of the base addition. The mixture is cooled down to 0° C. in one hour and stirred for 1 hour at 0° C. The white crystalline precipitate is filtered, the filter cake washed with ca. 2×10 ml ethanol 80% and the wet product dried in vacuo at 50° C. for 2 hours to yield 12.63 g of aripiprazole (form hydrate).

b)

5 g of the aripiprazole hydrate are recrystallized from 55 ml isopropanol using seed crystals of form X. There are obtained 4.5 g (93.6%) of form X of aripiprazole. Content of a dimer compound of formula VII as defined above: <0.05% (HPLC); Single other impurity: <0.05%

The invention claimed is:

1. A process for the production of aripiprazole or a pharmaceutically acceptable salt thereof comprising the steps of preparing and isolating an oxalic acid addition salt of aripiprazole or a solvate thereof and converting the oxalic acid addition salt or solvate thereof into aripiprazole in free form with less than 0.1% (w/w) of a compound of formula VII and optionally converting the free form aripiprazole into a pharmaceutically acceptable salt of aripiprazole.

2. A process for the production of aripiprazole or a pharmaceutically acceptable salt thereof comprising the steps of a) reacting a compound of formula

II with a compound of formula

III wherein X and Z are the same or different and each denote a halogen atom, or a group which is similar to halogen groups suitable to undergo a substitution reaction, to obtain a compound of formula

IV wherein X denotes as in formula III, b) reacting a compound of formula IV as obtained from step a) with a compound of formula

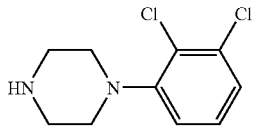

V to obtain a compound of formula

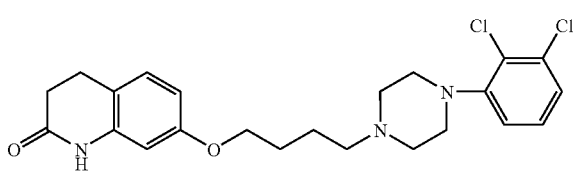

VI c) isolating the compound of formula VI as obtained in step b) in the form of an acid addition salt of formula

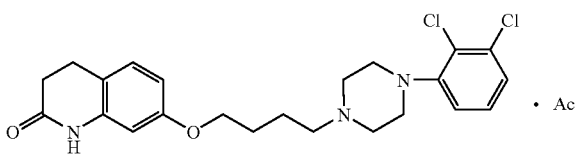 · Ac

VIII or a solvate thereof wherein Ac is oxalic acid, and d) converting an acid addition salt of formula VIII as obtained in step c) into a compound of formula VI to isolate aripiprazole in free form with less than 0.1% (w/w) of a compound of formula VII

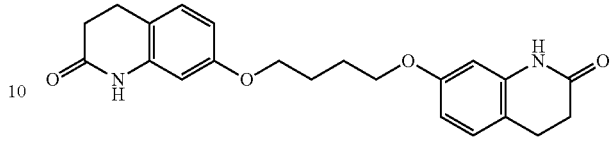

which is optionally further converted into a pharmaceutically acceptable salt of aripiprazole.

3. The process according to claim 2 which does not comprise any purification step of a compound of formula IV before reacting it with a compound of formula V.

4. The process according to claim 3 wherein aripiprazole in free form is isolated with less than 0.05% (w/w) of a compound of formula VII.

5. A process for the purification of aripiprazole by preparing an acid addition salt of formula VIII as defined in claim 2, isolating said acid addition salt and converting it into aripiprazole in free form.

6. The process according to claim 5 wherein the aripiprazole isolated in free form is an aripiprazole which is substantially pure in terms of crystalline form, by using appropriate seed crystals and containing less than 0.1% of a compound of formula VII.

7. The acid addition salt of formula VIII as defined in claim 1 which is used in the preparation of aripiprazole.

* * * * *

UNITED STATES PATENT AND TRADEMARK OFFICE
CERTIFICATE OF CORRECTION

PATENT NO. : 7,884,205 B2  Page 1 of 1
APPLICATION NO. : 11/883125
DATED : February 8, 2011
INVENTOR(S) : Johannes Ludescher et al.

It is certified that error appears in the above-identified patent and that said Letters Patent is hereby corrected as shown below:

In the Specification

Column 9, line 43, after "one" and before "at," insert --hour--.
Column 9, line 63, after "one" and before "at," insert --hour--.
Column 10, line 36, after "one" and before "two," insert --to--.
Column 11, line 26, after "one" and before "at," insert --hour-.
Column 11, line 64, after "one" and before "at," insert --hour--.
Column 12, line 60, after "MED," delete "und," and insert therefor --and--.
Column 13, line 5, after "MED," delete "und," and insert therefor --and--.

Signed and Sealed this
Fifth Day of July, 2011

David J. Kappos
*Director of the United States Patent and Trademark Office*